[19] United States Patent

Hansen et al.

[11] 4,272,282

[45] Jun. 9, 1981

[54] HERBICIDAL AGENTS BASED ON ACETANILIDES AND DICHLOROACETAMIDES

[75] Inventors: Hanspeter Hansen, Ludwigshafen; Karl Eicken, Wachenheim; Peter Plath, Ludwigshafen; Wolfgang Rohr, Mannheim; Bruno Wuerzer, Limburgerhof, all of Fed. Rep. of Germany

[73] Assignee: BASF Aktiengesellschaft, Fed. Rep. of Germany

[21] Appl. No.: 58,258

[22] Filed: Jul. 17, 1979

[30] Foreign Application Priority Data

Jul. 27, 1978 [DE] Fed. Rep. of Germany ....... 2832950

[51] Int. Cl.³ .................... A01N 43/56; A01N 37/18

[52] U.S. Cl. .......................................... 71/92; 71/88; 71/93; 71/94; 71/95; 71/105; 71/DIG. 1

[58] Field of Search .......................... 71/92, 118, 88

[56] References Cited

U.S. PATENT DOCUMENTS

| 4,021,224 | 5/1977 | Pallos et al. | 71/88 |
| 4,053,297 | 10/1977 | Richter | 71/88 |

FOREIGN PATENT DOCUMENTS

| 2648008 | 5/1978 | Fed. Rep. of Germany | 71/92 |
| 1454043 | 10/1976 | United Kingdom | 71/118 |

*Primary Examiner*—Glennon H. Hollrah
*Attorney, Agent, or Firm*—Keil & Witherspoon

[57] ABSTRACT

A herbicidal mixture containing a herbicidal substituted anilide and substituted dichloroacetamide as antidote therefor, is disclosed.

5 Claims, No Drawings

HERBICIDAL AGENTS BASED ON ACETANILIDES AND DICHLOROACETAMIDES

Herbicidal agents containing at least one substituted anilide of the formula

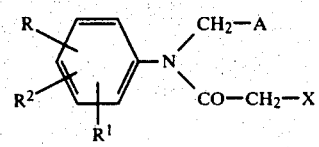

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes a salt of an azole containing 2 or 3 nitrogen atoms, as herbicidal active ingredient, and at least one dichloroacetamide of the formula

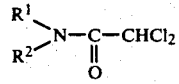

where $R^1$ and $R^2$ are identical or different and each denotes linear or branched alkyl of a maximum of 6 carbon atoms which is unsubstituted or substituted by alkoxy of a maximum of 4 carbon atoms or by cyano, $R^1$ and $R^2$ further denote linear or branched alkenyl or alkynyl of a maximum of 4 carbon atoms or cycloalkyl of 3 to 6 carbon atoms, or $R^1$ and $R^2$, together with the nitrogen atom whose substituents they are, form a 4- to 9-membered, saturated monocyclic or bicyclic ring which is unsubstituted or mono- or polysubstituted by linear or branched alkyl of a maximum of 4 carbon atoms, as antagonistic agent.

The ratio of acetanilide to dichloroacetamide is, whether applied separately or together, from 1:2 to 1:0.05 parts by weight. The agents are suitable for combating unwanted plant growth in Indian corn and cereals.

The present invention relates to herbicidal agents containing substituted acetanilides as herbicidal active ingredients and dichloroacetamides as antagonistic agents, and a process for the selective control of unwanted plant growth with these herbicidal agents.

Substituted acetanilides of the formula

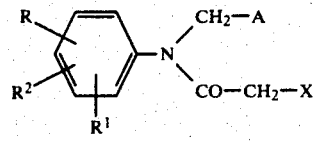

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes a salt of an azole containing 2 or 3 nitrogen atoms, have an excellent herbicidal action, but cause damage to crops such as Indian corn and Gramineae.

It was therefore the object of the invention to provide antagonistic agents which offset this poor tolerance of herbicidal acetanilides by certain crop plants.

Antagonistic agents (antidotes) are chemical compounds as a result of the presence of which the tolerance, by certain crop plants, of non-selective or insufficiently selective herbicidal active ingredients is increased without their action on unwanted plants being impaired.

Herbicidal agents containing, in addition to chloroacetanilides as herbicidal active ingredients, antagonistic dichloroacetamides have been disclosed in U.S. Pat. No. 4,053,297 and German Laid-Open Applications DE-OS Nos. 2,218,097 and 2,402,983.

For instance, German Laid-Open Application DE-OS No. 2,218,097 mentions combinations of the antagonistically active N,N-diallyldichloroacetamide and some herbicidal acetanilides, such as 2-chloro-2',6'-diethyl-N-(methoxymethyl)-acetanilide. However, this dichloroacetamide and structurally similar dichloroacetamides are predominantly used as antidotes in combination with herbicidal thiolcarbamates.

German Laid-Open Application DE-OS No. 2,402,983 and U.S. Pat. No. 4,053,297 relate to herbicidal agents containing dichloroacetamides known from German Laid-Open Application DE-OS No. 2,218,097, or dichloroacetamides structurally similar to them, and chloroacetanilides of different constitution. These agents are suitable for selective weed control in Indian corn.

We have now found that dichloroacetamides of the formula

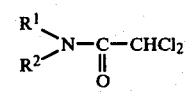

where $R^1$ and $R^2$ are identical or different and each denotes linear or branched alkyl of a maximum of 6 carbon atoms which is unsubstituted or substituted by alkoxy of a maximum of 4 carbon atoms or by cyano, $R^1$ and $R^2$ further denote linear or branched alkenyl or alkynyl of a maximum of 4 carbon atoms or cycloalkyl of 3 to 6 carbon atoms, or $R^1$ and $R^2$, together with the nitrogen atom whose substituents they are, form a 4- to 9-membered, saturated monocyclic or bicyclic ring which is unsubstituted or mono- or polysubstituted by linear or branched alkyl of a maximum of 4 carbon atoms, are excellently suited for increasing the tolerance of herbicidal substituted acetanilides of the formula I by crop plants. Herbicidal agents containing at least one substituted acetanilide of the formula II can be used in Indian corn and cereal crops. The good herbicidal action of the acetanilides is retained, and damage to the crop plants is prevented.

Acetanilides whose tolerance by crop plants can be increased by dichloroacetamides of the formula II are those in which R is hydrogen, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy and pentoxy;

$R^1$ and $R^2$ are hydrogen, halogen, such as fluorine, chlorine, bromine and iodine, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy, and pentoxy;

$R^2$ together with R is an alkylene chain of a maximum of 6 carbon atoms, linked in the o-position and unsubstituted or substituted by alkyl of a maximum of 4 carbon atoms, e.g., ethylene, trimethylene, tetramethylene, 1-methyltrimethylene, 1,1-dimethyltrimethylene, and 1,1-dimethyltetramethylene;

X is chlorine, bromine or iodine, preferably chlorine;

A is an azole attached via a ring nitrogen atom, e.g., pyrrole, pyrazole, imidazole, 1,2,4-triazole, 1,2,3-triazole, and tetrazole, which be mono- or polysubstituted by halogen, phenyl, alkyl, alkoxy, alkylthio or perfluoroalkyl, each of up to 4 carbon atoms, cyano, carboxy, or carbalkoxy with up to 4 carbon atoms in the alkoxy, or alkanoyl of up to 4 carbon atoms, the substituents being identical or different, such as 2,6-dimethylpyrrole, tetramethylpyrrole, 3(5)-methylpyrazole, 4-methylpyrazole, 3(5)-ethylpyrazole, 4-ethylpyrazole, 3(5)-iso-propylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, 4,5-dichloroimidazole, 2-ethyl-4,5-dichloroimidazole, 2-methyl-4,5-dichloroimidazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-yl-carboxylic acid ethyl ester, 1,2,3-triazol-4,5-yl-dicarboxylic acid dimethyl ester, 5-methyltetrazole, 5-chlorotetrazole, and tetrazolyl-5-carboxylic acid ethyl ester.

Furthermore, the radical A may, when the optionally substituted azole contains 2 or 3 nitrogen atoms, also be attached in a salt-like manner to one of the usual strong inorganic or organic acids, e.g., hydrochloric acid, hydrobromic acid, nitric acid, sulfuric acid, tetrafluoboric acid, fluosulfonic acid, and formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid and perfluorohexanesulfonic acid, and an arylsulfonic acid, e.g. dodecylbenzenesulfonic acid.

Preferred acetanilides are those which bear methyl or ethyl in the 2- and 6-positions on the phenyl ring and hydrogen, methyl or ethyl in the 3-position; suitable azoles are pyrazole, imidazole, triazole and tetrazole, which are unsubstituted or substituted by lower alkyl, alkoxy, carbalkoxy, cyano or halogen.

In particular, the herbicidal agents according to the invention contain the following acetanilides: 2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methylpyrazol-1-yl-methyl)-acetanilide, 2-chloro-2-methyl-6-ethyl-N-(4-methoxypyrazol-1-yl-methyl)-acetanilide, 2-chloro-2'-methyl6'-ethyl-N-(3(5)-methylpyrazol-1-yl)-acetanilide, 2-chloro-2',6'-dimethyl-N-(3,5-dimethylpyrazol-1-yl-methyl)-acetanilide, 2-chloro-2',6'-dimethyl-N-(1,2,4-triazol-1-yl-methyl)-acetanilide, 2-chloro-2',6'-dimethyl-N-(4-chloropyrazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethylpyrazol-1-yl-methyl)-acetanilide, 2-chloro-2',6'-diethyl-N-(3,5-dimethylpyrazol-1-yl-methyl)-acetanilide, 2-chloro-2',3',6'-trimethyl-N-(3,5-dimethylpyrazol-1-yl-methyl)-acetanilide, 2-chloro-2',6'-diethyl-N-(4-methylpyrazol-1-yl-methyl)-acetanilide, 2-chloro-2'-methyl-6'-ethyl-N-(4-methylpyrazol-1-yl-methyl)-acetanilide, 2-chloro-2',3',6'-trimethyl-N-(4-methylpyrazol-1-yl-methyl)-acetanilide, 2-chloro-2',6'-dimethyl-N-(3-(5)-methylpyrazol-1-yl-methyl)-acetanilide, 2-chloro-2',6'-diethyl-N-(3-(5)-metnhylpyrazol-1-yl-methyl)-acetanilide, 2-chloro-2',6'-dimethyl-N-(4-methoxypyrazol-1-yl-methyl)-acetanilide, 2-chloro-2',6'-diethyl-N-(pyrazol-1-yl-methyl)-acetanilide, 2-chloro-2',6'-dimethyl-N-(4,5-dichloroimidazol-1-yl-methyl)-acetanilide, 2-chloro-2'-methyl-6'-ethyl-N-(4,5-dichloroimidazol-1-yl-methyl)-acetanilide, 2-chloro-2'-methyl-6'-ethyl-N-(2-ethyl-4,5-dichloroimidazol-1-yl-methyl)-acetanilide, 2-chloro-2',6'-diethyl-N-(4,5-dichloroimidazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide and 2-chloro-2',3',6'-trimethyl-N-(1,2,4-triazol-1-yl-methyl)-acetanilide.

The acetanilides of the formula I are disclosed in German Laid-Open Application DE-OS No. 2,648,008 and DE-OS No. 2,744,396. They may be obtained by reaction of 2-halo-N-halomethylacetanilides of the formula III with a 1H-azole of the formula H-A in accordance with the following equation:

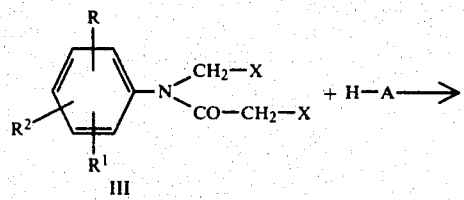

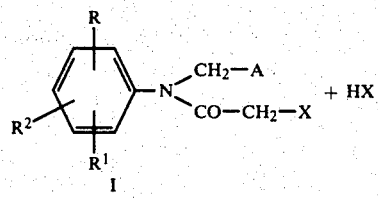

R, R¹, R² and X have the above meanings and A denotes an azole linked via a ring nitrogen atom and which may be mono- or poly-substituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms.

Suitable antagonistic agents are dichloroacetamides of the formula II in which the substituents $R^1$ and $R^2$ are identical or different and denote linear or branched alkyl of a maximum of 6 carbon atoms, e.g., methyl, ethyl, n-propyl, isopropyl, n-butyl, isobutyl, sec-butyl, tert-butyl, n-hexyl, and 1,4-dimethyl-n-butyl, linear or branched alkenyl or alkynyl of a maximum of 4 carbon atoms, e.g., allyl, propargyl, and 1-methylbutyn-2-yl, or cycloalkyl of 3 to 6 carbon atoms, e.g., cyclopropyl and cyclohexyl. The alkyl radicals are unsubstituted or substituted by alkoxy of a maximum of 4 carbon atoms, e.g., methoxy and ethoxy, or by cyano. The alkoxy group is preferably in the terminal position to the carbon radicals.

$R^1$ and $R^2$ may also, together with the nitrogen atom whose substituents they are, form a 4- to 9-membered, saturated mono- or bicyclic ring. This heterocycle is unsubstituted or mono- or polysubstituted by linear or branched alkyl of a maximum of 4 carbon atoms. Examples of such rings are piperidinyl, alkylpiperidinyl, e.g., 3,5-diethylpiperidinyl, 2,5-dimethylpyrrolidinyl, azetidinyl, alkylazetidinyl, e.g., 2.2.4-trimethylazetidinyl, hexahydroazepinyl, alkylhexahydroazepinyl, e.g., 3.5.5/3.3.5-trimethylhexahydroazepinyl and 2,3-dimethylhexahydroazepinyl, aza-bicyclo-[3.2.2]-nonyl, alkyl-aza-bicyclo-octyl, e.g., trimethyl-aza-bicyclo-[3.2.1]-octyl, and aza-bicyclo-[3.2.0]-heptyl.

A preferred antagonistic agent is N-isopropyl-N-propargyldichloroacetamide.

The dichloroacetamides of the formula II may be obtained by reaction of amines of the formula

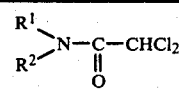

where $R^1$ and $R^2$ have the above meanings, with dichloroacetyl chloride. The reaction is carried out in conventional manner in the presence of an agent which binds hydrogen chloride, in an inert solvent or diluent.

Examples of agents which bind hydrogen chloride are inorganic bases, such as alkali metal carbonates, alkali metal bicarbonates and alkali metal hydroxides, and organic bases, such as tertiary amines, e.g., trialkylamines, and especially triethylamine.

Suitable inert solvents or diluents are hydrocarbons, such as toluene and cyclohexane, halogenated hydrocarbons, such as methylene chloride and ethylene chloride, and ethers, such as dioxane and tetrahydrofuran.

The following examples illustrate the preparation of the dichloroacetamides.

EXAMPLE 1

118 g of isopropylpropargylamine and 123 g of triethylamine are dissolved in 670 ml of toluene. While cooling and at room temperature, a solution of 180 g of dichloroacetyl chloride in 450 ml of toluene is dripped into this solution. The mixture is allowed to react for 1 hour before being filtered, and the filtrate is washed with water. The residue remaining after removal of the solvent is washed with petroleum ether. There is obtained 214 g (84% of theory) of N-isopropyl-N-propargyldichloroacetamide; b.p. (0.013 mbar): 80°–82° C.; m.p.: 58°–59° C.

EXAMPLE 2

20.2 g of triethylamine is added to a solution of 20 g of hexamethyleneimine in 150 ml of toluene. 30 g of dichloroacetyl chloride is then dripped in at 0° C. After the mixture has been stirred for 8 hours at 20° C. it is filtered, and the filtrate is extracted with dilute hydrochloric acid, neutralized with sodium bicarbonate solution, and dried over sodium sulfate. Concentration of the residue under reduced pressure gives an oil, which crystallizes upon trituration in n-hexane. The yield is 35 g (83% of theory) of 1-dichloroacetylhexamethyleneimine; m.p.: 57°–58° C.

The following dichloroacetamides may be obtained analogously:

$$\begin{matrix} R^1 \\ R^2 \end{matrix} \!\!\!\!\!\! N-\underset{\underset{O}{\|}}{C}-CHCl_2$$

| No. | R¹ | R² | b.p./m.p./$n_D$ |
|---|---|---|---|
| 1 | CH₂=CH—CH₂— | CH₂=CH—CH₂— | $n_D^{30}$: 1.4990 |
| 2 | HC≡C—CH₂— | n-C₃H₇ | $n_D^{26}$: 1.4978 |
| 3 | HC≡C—CH₂— | (CH₃)₂CH—CH₂—CH(CH₃)— | $n_D^{25}$: 1.4889 |
| 4 | HC≡C—CH₂— | CH₃ | $n_D^{25}$: 1.5090 |
| 5 | i-C₃H₇ | C₂H₅ | $n_D^{25}$: 1.4849 |
| 6 | i-C₃H₇ | i-C₃H₇ | m.p.: 62–65° C. |
| 7 | n-C₄H₉ | C₂H₅ | $n_D^{25}$: 1.4802 |
| 8 | sec.-C₄H₉ | CH₃ | $n_D^{25}$: 1.4820 |
| 9 | i-C₄H₉ | CH₃ | $n_D^{25}$: 1.4820 |
| 10 | sec.-C₄H₉ | HC≡C—CH(CH₃)— | $n_D^{25}$: 1.4923 |
| 11 | n-C₄H₉ | CH₃ | $n_D^{25}$: 1.4835 |

-continued

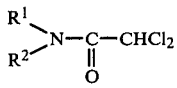

| No. | R¹ | R² | b.p./m.p./$n_D$ |
|---|---|---|---|
| 12 | HC≡C—CH₂— | sec.-C₄H₉ | $n_D^{25}$: 1.4960 |
| 13 | —(CH₂)₃— | | m.p.: 37–39° C. |
| 14 | —(CH₂)₄— | | $n_D^{25}$: 1.5190 |
| 15a | —(CH₂)₅— | | m.p.: 41–42° C. |
| 15b | —CH₂—CH—(CH₂)₂—CH—CH₂—<br>　　　＼　　　　　／<br>　　　　CH₂—CH₂ | | m.p.: 101–102° C. |
| 16 | —CH(CH₃)—CH₂—C(CH₃)₂— | | m.p.: 48–49° C. |
| 17 | —CH₂—CH(CH₃)—CH₂—C(CH₃)₂—CH₂—CH—<br>　　　　　　　　＼　　　　／<br>　　　　　　　　　CH₂ | | m.p.: 82–84° C. |
| 18 | —CH(CH₃)—(CH₂)₂—CH(CH₃)— | | m.p.: 61–65° C. |
| 19 | —CH₂—CH(C₂H₅)—CH₂—CH(C₂H₅)—CH₂— | | $n_D^{25}$: 1.5003 |
| 20 | H₃CO—CH₂—CH₂ | H₃CO—CH₂—CH₂— | b.p.: 132° C./0.4 mbar |
| 21 | H₃CO—CH₂—CH(CH₃)— | CH₃ | b.p.: 105° C./0.53 mbar |
| 22 | H₃CO—CH₂—CH(CH₃)— | i-C₃H₇ | b.p.: 104° C./0.67 mbar |
| 23 | ▷— | —CH₂—C≡CH | m.p.: 73–75° C. |
| 24 | tert.-C₄H₉ | —CH₂—C≡CH | $n_D^{25}$: 1.4950 |
| 25 | i-C₃H₇ | ▷— | $n_D^{25}$: 1.4936 |
| 26 | C₆H₁₁ | ▷— | m.p.: 104–106° C. |
| 27 | C₆H₁₁ | —CH₂—CN | m.p.: 98–103° C. |
| 28 | C₂H₅—CH(CH₃) | —CH₂—CN | $n_D^{25}$: 1.5028 |
| 29 | tert.-C₄H₉ | —CH₂—CN | m.p.: 117–119° C. |
| 30 | —CH₂—CH　　CH—CH₂—<br>　　　｜　　　｜<br>　　　CH₂—CH₂ | | b.p.: 110–112° C./<br>0.013 mbar |

The antagonistic dichloroacetamides of the formula II themselves have scarcely any influence; if at all, on the germination and growth of crop and unwanted plants, even at application rates well above those required for an antagonistic effect. However, they are capable of considerably reducing the phytotoxicity of the herbicidal acetanilides of the formula I to crop plants such as Indian corn, or of eliminating it completely.

In the case of herbicidal acetanilides which are less agressive to crop plants, lesser amounts of antagonistic compounds, or the addition of compounds having a lower antagonistic activity, are sufficient. The ratio of acetanilide to dichloroacetamide may vary within wide limits, and depends both on the acetanilide and the dichloroacetamide. Suitable ratios of herbicidal active ingredient to antagonistic compound are from 1:2 to 1:0.05 parts by weight.

Acetanilides and dichloroacetamides may be incorporated into the soil either together or separately and before or after sowing. With acetanilides of the formula, the commonest method is to apply them to the surface of the soil immediately after sowing, or in the period between sowing and emergence of the young plants. It is also possible to apply them during emergence and shortly thereafter. In each instance, the antagonistic agent may be applied simultaneously with the herbicidal active ingredient. It is also possible to apply the compounds separately—either the antagonist first and then the herbicidal active ingredient, or vice versa—provided that, if the herbicidal active ingredient is applied first, not too much time elapses before the antagonist is applied as otherwise the crop plants may be damaged. The active ingredient and antagonist may be suspended, emulsified or dissolved in a spray liquor or may be in granular form, and may be formulated together or separately. It is also feasible to treat the seed with the antagonist before sowing. The herbicidal active ingredient is then applied on its own in the usual manner.

The novel herbicidal agents may contain, in addition to acetanilide and dichloroacetamide, other herbicidal or growth-regulating active ingredients of different chemical structure, e.g., 2-chloro-4-ethylamino-6-isopropylamino-1,3,5-triazine, without the antagonistic effect being impaired.

The agents according to the invention, or, when applied separately, the herbicidal active ingredients and the antidote are applied for instance in the form of directly sprayable solutions, powders, suspensions (including high-percentage aqueous, oily or other suspensions), dispersions, emulsions, oils dispersions, pastes, dusts, broadcasting agents, or granules by spraying, atomizing, dusting, broadcasting or watering. The forms of application depend entirely on the purpose for which the agents are being used; in any case they should ensure very fine distribution of the agents according to the invention or their individual components.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote, as such or dissolved in an oil or solvent, may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of herbicidal active ingredient and/or antidote. Application rates are from 0.2 to 5 kg of herbicidal active ingredient per hectare. This amount of herbicidal active ingredient is applied, together or separately, with such an amount of antidote to give a ratio of herbicidal active ingredient to antagonist of from 1:2 to 1:0.05 parts by weight.

Examples of formulations are given below.

I. 3 parts by weight of a mixture of 8 parts by weight of 2-chloro-2',6'-dimethyl-N-(pyrazol-1-yl-methyl)-acetanilide and 1 part by weight of N,N-diallyldichloroacetamide is intimately mixed with 97 parts by weight of particulate kaolin. A dust is obtained containing 3% by weight of the mixture of active ingredient+antidote.

II. 30 parts by weight of a mixture of 1 part by weight of 2-chloro-2'-methyl-6'-ethyl-N-(1,2,4-trizaol-1-yl-methyl)-acetanilide and 1 part by weight of N-propargyl-N-isopropyldichloroacetamide is intimately mixed with a mixture consisting of 92 parts by weight of powdered silica gel and 8 parts by weight of paraffin oil which has been sprayed onto the surface of this silica gel. A formulation is obtained having good adherence.

III. 20 parts by weight of a mixture of 1 part by weight of 2-chloro-2'-methyl-6'-ethyl-N-(4,5-dichloroimidazol-1-yl-methyl)-acetanilide and 2 parts by weight of N,N-diallyldichloroacetamide is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the mixture of active ingredient+antidote.

IV. 20 parts by weight of a mixture of 4 parts by weight of 2-chloro-2',6'-dimethyl-N-(4-methoxypyrazol-1-yl-methyl)-acetanilide and 1 part by weight of N-propargyl-N-n-propyldichloroacetamide is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the mixture of active ingredient+antidote.

Greenhouse experiments and experiments in the open show that the use of the herbicidal agents according to the invention increases the tolerance of the herbicidal acetanilides by the crop plants without the herbicidal action being affected.

I. Greenhouse experiments

Plastic boxes 51 cm long, 32 cm wide and 6 cm deep were filled with loamy sand (pH:6) containing about 1.5% humus. Indian corn (Zea mays) was sown shallow, in rows, in this substrate. Echinochloa crus-galli and *Alopecurus myosuroides* were scattered at random as unwanted plants. The non-sterilized soil also additionally contained viable weed seeds which contributed to the weed population. A field with crop plants growing in it and infested with weeds was thus simulated.

The active ingredients and the antagonistic compounds were applied separately and in the mixtures given below. They were emulsified or suspended in water as vehicle and the liquor was sprayed through finely distributing nozzles onto the soil surface, either immediately after sowing or prior to emergence of the test plants. In some cases, the agents were also incorporated into the soil before the crop plants were sown. After sowing and treatment the boxes were sprinkler-irrigated and covered with transparent plastic hoods until the plants emerged. These measures ensured that the plants germinated and took root uniformly. The boxes were set up in the greenhouse at from 18° to 30° C.

These greenhouse experiments were monitored until 3 to 5 Indian corn leaves had developed. No more damage due to the herbicidal agents was to be expected after this stage, a fact which was confirmed by the experiments in the open.

The scale for assessing the action of the agents was 0 to 100, 0 denoting normal emergence and developement of the plants, with reference to the untreated control, and 100 denoting non-germination or withering of the plants. It should be borne in mind here that, for instance in Indian corn, odd crippled or retarded plants may occur even under completely normal conditions and without any chemical treatment.

II. Experiments in the open

These experiments were carried out on small plots in loamy sand and loam (pH:5 to 6) containing from 1 to 1.5% humus. Preemergence treatment was carried out either immediately after the crop plants had been sown, or at the latest 3 days later. The weed flora was made up of numerous varieties and was natural. However, only the dominating representatives are given in the tables. The herbicidal active ingredients and antagonists, and combinations thereof, were emulsified or suspended in water as vehicle, and applied by means of a motor-driven plot spray mounted on a tractor. Where no rain fell, the plots were sprinkled to ensure normal emergence of crop plants and weeds. All the experiments were run for several months, enabling the development of the crop plants up to seed formation to be observed. The action of the agents was also assessed on the 0 to 100 scale.

Results

The results given in the following tables show that the antagonistic dichloroacetamides of the formula II, when used in combination with the herbicidal chloroacetanilides of the formula I, counterbalance the non-tolerance of these herbicidal active ingredients by the crop plants.

As a result of the shallow sowing of the crop plants and the more favorable conditions for herbicidal action, the damage caused by the herbicidal active ingredients was much greater in the greenhouse than in the open. Consequently, the antagonistic compounds were put to a harder test in the greenhouse than in the open.

TABLE 1

List of plant names

| Botanical name | Common name |
| --- | --- |
| Alopecurus myosuroides | slender foxtail |
| Chenopodium album | lambsquarters |
| Echinochloa crus galli | barnyardgrass |
| Zea mays | Indian corn |

TABLE 2

List of the herbicidal acetanilides employed in the biological examples

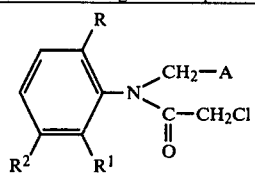

| No. | A | R | $R^1$ | $R^2$ |
| --- | --- | --- | --- | --- |
| I | -N(pyrazol-1-yl) | $CH_3$ | $CH_3$ | H |

TABLE 2-continued

List of the herbicidal acetanilides employed in the biological examples

| No. | A | R | $R^1$ | $R^2$ |
| --- | --- | --- | --- | --- |
| II | -N(pyrazol-1-yl) | $C_2H_5$ | $CH_3$ | H |
| III | -N(3-methylpyrazol-1-yl) | $CH_3$ | $CH_3$ | H |
| IV | -N(4-methoxypyrazol-1-yl) | $C_2H_5$ | $CH_3$ | H |
| V | -N(3-methylpyrazol-1-yl) | $C_2H_5$ | $CH_3$ | H |
| VI | -N(3,5-dimethylpyrazol-1-yl) | $CH_3$ | $CH_3$ | H |
| VII | -N(1,2,4-triazol-1-yl) | $CH_3$ | $CH_3$ | H |
| VIII | -N(4-chloropyrazol-1-yl) | $CH_3$ | $CH_3$ | H |
| IX | -N(pyrazol-1-yl) | $CH_3$ | $CH_3$ | $CH_3$ |

TABLE 3

List of the dichloroacetamides employed in the biological examples

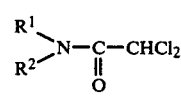

| Designation | $R^1$ | $R^2$ |
| --- | --- | --- |
| A | $-CH_2-CH=CH_2$ | $-CH_2CH=CH_2$ |
| B | $-CH_2-C\equiv CH$ | $n-C_3H_7$ |
| C | $-CH_2-C\equiv CH$ | $i-C_3H_7$ |

TABLE 4

Improvement in the tolerance by Indian corn of 2-chloro-2',6'-dimethyl-N-(pyrazol-1-yl-methyl)-acetanilide by means of antagonistic dichloroacetamides; preemergence treatment in the greenhouse

| Herbicidal active ingredient | Antagonistic compound | Appln. rate [kg/ha] | Test plants and % damage | |
|---|---|---|---|---|
| | | | Crop plant Zea mays | unwanted plant Echinochloa crus galli |
| I | — | 1.0 | 63 | 100 |
| | | 2.0 | 78 | 100 |
| | A | 2.0 | 4 | 8 |
| I | + A | 1.0 + 0.125 | 34 | 100 |
| | | 1.0 + 0.25 | 22 | 99 |
| | | 2.0 + 0.5 | 43 | 100 |
| | B | 2.0 | 0 | 0 |
| I | + B | 1.0 + 0.25 | 41 | 99 |
| | | 1.0 + 1.0 | 25 | 99 |
| | | 2.0 + 0.5 | 50 | 100 |
| | C | 2.0 | 3 | 0 |
| I | + C | 1.0 + 0.125 | 17 | 98 |
| | | 1.0 + 0.25 | 13 | 97 |
| | | 1.0 + 0.5 | 7 | 96 |
| | | 1.0 + 1.0 | 12 | 100 |
| | | 2.0 + 0.5 | 23 | 100 |

TABLE 5

Improvement in the tolerance by crop plants of herbicidal acetanilides by means of antagonistic dichloroacetamides; preemergence treatment in the greenhouse

| Herbicidal active ingredient | Antagonistic compound | Appln. rate [kg/ha] | Crop plant | Unwanted plants | |
|---|---|---|---|---|---|
| | | | Zea mays | Alopecurus myosuroides | Echinochloa crus galli |
| II | — | 1.0 | 50 | 95 | 99 |
| | | 2.0 | 63 | 96 | 98 |
| II | + C | 1.0 + 0.125 | 5 | 98 | 98 |
| | | 1.0 + 0.25 | 3 | 96 | 98 |
| | | 1.0 + 2.0 | 5 | 85 | 98 |
| | | 2.0 + 0.5 | 5 | 98 | 99 |
| III | — | 1.0 | 30 | 88 | 99 |
| | | 2.0 | 47 | 99 | 99 |
| III | + C | 1.0 + 0.125 | 2 | 80 | 99 |
| | | 1.0 + 0.25 | 2 | 88 | 99 |
| | | 1.0 + 1.0 | 7 | 84 | 99 |
| | | 2.0 + 0.5 | 3 | 100 | 100 |
| IV | — | 1.0 | 17 | 90 | 99 |
| | | 2.0 | 42 | 90 | 99 |
| IV | + C | 1.0 + 0.125 | 2 | 89 | 99 |
| | | 1.0 + 1.0 | 5 | 88 | 99 |
| | | 2.0 + 0.5 | 6 | 92 | 100 |
| V | — | 1.0 | 60 | 90 | 99 |
| | | 2.0 | 65 | 94 | 99 |
| V | + C | 1.0 + 0.25 | 7 | 90 | 99 |
| | | 1.0 + 1.0 | 5 | 92 | 99 |
| | | 2.0 + 0.5 | 7 | 98 | 99 |
| VI | — | 1.0 | 73 | 98 | 99 |
| | | 2.0 | 85 | 98 | 99 |
| VI | + C | 1.0 + 1.0 | 18 | 93 | 98 |
| VII | — | 1.0 | 35 | 94 | 99 |
| | | 2.0 | 55 | 98 | 99 |
| VII | + C | 1.0 + 1.0 | 2 | 84 | 99 |
| VIII | — | 1.0 | 12 | 85 | 98 |
| | | 2.0 | 25 | 90 | 99 |
| VIII | + C | 1.0 + 0.125 | 5 | 80 | 98 |
| | | 2.0 + 0.25 | 2 | 96 | 98 |
| IX | — | 1.0 | 80 | 90 | 99 |
| | | 2.0 | 82 | 95 | 100 |
| IX | + C | 1.0 + 0.125 | 5 | 98 | 98 |
| | | 1.0 + 1.0 | 2.5 | 98 | 98 |
| | | 2.0 + 0.5 | 5 | 99 | 98 |

0 = no damage, 100 = non-emergence, or plants withered

TABLE 6

Improvement in the tolerance by Indian corn of 2-chloro-2',6'-dimethyl-N-(pyrazol-1-yl-methyl)-acetanilide by means of antagonistic dichloroacetamides; preemergence treatment in the open

| Herbicidal active ingredient | Antagonistic compound | Appln. rate [kg/ha] | Crop plant | Unwanted plants | |
|---|---|---|---|---|---|
| | | | Zea mays | Echinochloa crus galli | Chenopodium album |
| I | — | 2.0 | 37 | 100 | 99 |
| | | 3.0 | 39 | 100 | 100 |
| | | 4.0 | 55 | 100 | 100 |
| | A | 4.0 | 0 | 0 | 0 |
| I | + A | 2.0 + 0.5 | 19 | 100 | 100 |
| | | 2.0 + 1.0 | 10 | 100 | 100 |
| | | 3.0 + 1.0 | 25 | 100 | 100 |
| | | 4.0 + 1.0 | 42 | — | — |
| | C | 4.0 | 0 | 0 | 0 |
| I | + C | 2.0 + 0.5 | 7 | 100 | 100 |
| | | 2.0 + 1.0 | 6 | 100 | 100 |
| | | 3.0 + 1.0 | 18 | 100 | 100 |
| | | 4.0 + 1.0 | 18 | 100 | 100 |

0 = normal emergence and growth, 100 = non-emergence, or plants withered

We claim:

1. A herbicidal agent for the selective control of unwanted plant growth in corn, said agent containing and effective amount of a substituted acetanilide of the formula

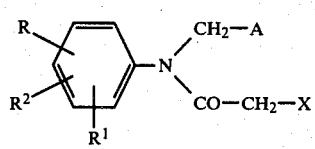

where R denotes hydrogen or linear or branched alkyl of up to 5 carbon atoms, $R^1$ denotes hydrogen or linear or branched alkyl of up to 5 carbon atoms, $R^2$ denotes hydrogen or linear or branched alkyl of up to 5 carbon atoms, X denotes chlorine or bromine, and A denotes pyrazole which is attached via a ring nitrogen atom and may be mono- or polysubstituted by halogen, alkyl or alkoxy, each of up to 4 carbon atoms, or A denotes a salt of a pyrazole, as a herbicidal active ingredient, and N-isopropyl-N-propargyl-dichloroacetamide as an antagonistic agent, the ratio of the acetanilide of formula I to the antagonistic agent being from 1:2 to 1:0.125 parts by weight.

2. A herbicidal agent as claimed in claim 1, wherein the herbicidal active ingredient is 2-chloro-2'6'-dimethyl-N-(pyrazol-1-yl-methyl)-acetanilide.

3. A process for the selective control of unwanted plant growth, wherein an effective amount of a herbicidal agent as claimed in claim 1 is applied before, during or after sowing of the corn, or before or during emergence of the corn.

4. A process for the selective control of unwanted plant growth, wherein a herbicidally effective amount of a substituted acetanilide of the formula I and an antidotally effective amount of N-isopropyl-N-propargyl-dichloroacetamide are applied before, during or after sowing of the corn, or before or during emergence of the corn, either simultaneously or one after the other in any order, the ratio of the acetanilide to N-isopropyl-N-propargyl-dichloroacetamide being from 1:2 to 1:0.125 parts by weight.

5. A process for the selective control of unwanted plant growth according to claim 4, wherein the seed of the corn is treated with dichloroacetamide.

* * * * *